United States Patent
Hirai et al.

(10) Patent No.: US 11,830,184 B2
(45) Date of Patent: Nov. 28, 2023

(54) MEDICAL IMAGE PROCESSING DEVICE, MEDICAL IMAGE PROCESSING METHOD, AND STORAGE MEDIUM

(71) Applicant: Toshiba Energy Systems & Solutions Corporation, Kawasaki (JP)

(72) Inventors: Ryusuke Hirai, Shinagawa (JP); Akiyuki Tanizawa, Kawasaki (JP); Shinichiro Mori, Chiba (JP); Keiko Okaya, Setagaya (JP)

(73) Assignee: Toshiba Energy Systems & Solutions Corporation, Kawasaki (JP)

( * ) Notice: Subject to any disclaimer, the term of this patent is extended or adjusted under 35 U.S.C. 154(b) by 671 days.

(21) Appl. No.: 17/045,911

(22) PCT Filed: Mar. 8, 2019

(86) PCT No.: PCT/JP2019/009394
§ 371 (c)(1),
(2) Date: Oct. 7, 2020

(87) PCT Pub. No.: WO2019/198394
PCT Pub. Date: Oct. 17, 2019

(65) Prior Publication Data
US 2021/0035293 A1    Feb. 4, 2021

(30) Foreign Application Priority Data

Apr. 9, 2018  (JP) .................. 2018-075024

(51) Int. Cl.
*G06T 7/00* (2017.01)
*A61N 5/10* (2006.01)

(52) U.S. Cl.
CPC ............ *G06T 7/0012* (2013.01); *A61N 5/103* (2013.01); *A61N 5/1049* (2013.01);
(Continued)

(58) Field of Classification Search
CPC ......... G06T 7/0012; G06T 2207/10081; G06T 2207/10124; G06T 2207/20081;
(Continued)

(56) References Cited

U.S. PATENT DOCUMENTS 6,819,790 B2   11/2004   Suzuki et al.
8,379,794 B2    2/2013   Poulsen et al.
(Continued)

FOREIGN PATENT DOCUMENTS

JP   2011-500263 A   1/2011
JP   2017-42247 A    3/2017
JP   2018-29852 A    3/2018

OTHER PUBLICATIONS

Ruijiang Li, et al., "A Bayesian approach to real-time 3D tumor localization via monoscopic x-ray imaging during treatment delivery," Medical Physics, vol. 38, No. 7, Jul. 2011, pp. 4205-4214.

*Primary Examiner* — Lewis G West
(74) *Attorney, Agent, or Firm* — Oblon, McClelland, Maier & Neustadt, L.L.P.

(57) ABSTRACT

A medical image processing device includes a first position acquirer, a first converter, a first likelihood image generator, and a learner. The first position acquirer is configured to acquire, as first positions, target positions in plural first images. The first converter is configured to convert the first positions to second positions by expanding movement in a second direction intersecting a first direction based on movement over time of the first positions. The first likelihood image generator is configured to generate a first likelihood image showing a distribution of likelihood of the second positions. The learner is configured to output a model using the plural first images and the first likelihood image as training data, and upon receiving part or all of a transparent image, derives a second likelihood image showing a distri- (Continued)

bution of likelihood indicating probability of the part or all of the transparent image corresponding to the second positions.

11 Claims, 9 Drawing Sheets

(52) U.S. Cl.
CPC ............... *A61N 2005/1062* (2013.01); *G06T 2207/10081* (2013.01); *G06T 2207/10124* (2013.01); *G06T 2207/20081* (2013.01); *G06T 2207/20084* (2013.01); *G06T 2207/30096* (2013.01)

(58) Field of Classification Search
CPC . G06T 2207/20084; G06T 2207/30096; G06T 7/262; G06T 2207/10116; G06T 7/00; A61N 5/103; A61N 5/1049; A61N 2005/1062; A61N 5/1067; A61N 2005/1051; A61N 2005/1061; A61B 6/4266; A61B 6/5217; A61B 6/12
See application file for complete search history.

(56) References Cited

U.S. PATENT DOCUMENTS

| | | | |
|---|---|---|---|
| 2006/0268109 A1* | 11/2006 | Miyoshi | G06F 3/0325 348/143 |
| 2007/0154078 A1* | 7/2007 | He | G06F 18/00 382/135 |
| 2009/0110238 A1 | 4/2009 | Li et al. | |
| 2010/0172469 A1* | 7/2010 | Poulsen | A61B 6/583 378/65 |
| 2012/0207359 A1* | 8/2012 | Konukoglu | G06V 10/764 382/128 |
| 2012/0288198 A1* | 11/2012 | Tojo | G06V 20/52 382/173 |
| 2013/0301882 A1* | 11/2013 | Kawaguchi | G06V 40/20 382/103 |
| 2017/0032538 A1 | 2/2017 | Ernst et al. | |
| 2017/0061641 A1* | 3/2017 | Inoue | G06T 7/246 |
| 2017/0272661 A1* | 9/2017 | Tsubusaki | G01S 3/00 |
| 2018/0193672 A1 | 7/2018 | Hirai et al. | |
| 2019/0065900 A1* | 2/2019 | Nishino | G06T 7/246 |
| 2020/0160535 A1* | 5/2020 | Ali Akbarian | G06N 5/046 |
| 2020/0242407 A1* | 7/2020 | Gandhi | G06V 30/19147 |
| 2021/0012500 A1* | 1/2021 | Miyazaki | A61B 6/12 |
| 2021/0137485 A1* | 5/2021 | Sakata | A61N 5/1049 |
| 2022/0054862 A1* | 2/2022 | Hirai | A61N 5/1067 |

* cited by examiner

MEDICAL IMAGE PROCESSING DEVICE, MEDICAL IMAGE PROCESSING METHOD, AND STORAGE MEDIUM

TECHNICAL FIELD

Embodiments of the present invention relate to a medical image processing device, a medical image processing method, and a program.

Priority is claimed on Japanese Patent Application No. 2018-075024, filed Apr. 9, 2018, the content of which is incorporated herein by reference.

BACKGROUND ART

Conventionally, a radiation treatment method of applying radiation to a tumor of a patient to treat the patient has been disclosed. Radiation needs to be accurately applied to the position of a tumor. This is because there are cases in which, when radiation is applied to normal tissues in the body of a patient, the normal tissues are also affected. Accordingly, the position of a tumor in the body of a patient is three-dimensionally detected by performing computed tomography (CT) in advance and an irradiation direction and irradiation intensity are planned such that irradiation of normal tissues is reduced. In radiation treatment, it is necessary to align a relative position of a patient with respect to a device (hereinafter, simply a patient position) at the time of treatment planning and treatment because radiation is applied according to a treatment plan.

To align positions of a tumor, a bone, and the like in the body of a patient with those at the time of treatment planning, image collation of a transparent image of the inside of the body of a patient lying on a bed immediately before treatment and a digitally reconstructed radiograph (DRR) that is a transparent image virtually reconstructed from a three-dimensional CT image captured at the time of treatment planning is performed to obtain displacement of the patient position between the images, and position alignment for moving the bed on the basis of the displacement is performed. The displacement of the patient position is obtained by searching for a position of a CT image in which a DRR most similar to the transparent image is reconstructed. A plurality of methods of automating the search through a computer have been proposed. However, a user (doctor or the like) ultimately checks the transparent image and the DRR image with respect to the automatically searched result to confirm that displacement of the patient position is sufficient small. Then, the application of radiation is performed after a confirmation is performed by the user.

In a case where a tumor in the body of a patient is present in an organ that moves due to movement of breathing and heartbeat, such as the lungs or liver, the position of a tumor under irradiation needs to be identified. Identification methods include a method of continuously capturing transparent images of a patient under irradiation and tracing the tumor in the sequential transparent images, a method of indirectly identifying the position of a tumor by tracking a marker positioned inside the body of a patient when a tumor is not clearly imaged in a transparent image, and the like. Irradiation methods include tracking irradiation of tracking the position of a tumor and irradiating it and ambush irradiation of irradiating a tumor when the tumor reaches a certain position at the time of treatment planning. These irradiation methods are referred to as a respiration synchronized irradiation because irradiation is synchronized with respiration of a patient.

There is a method of acquiring an image pattern of a tumor in advance and searching for the position of a similar image pattern in a transparent image captured at the time of treatment to identify the position of the tumor as a method of tracing a tumor captured in a transparent image. In this method, an image including a tumor and an image not including the tumor are prepared, a discriminator that discriminates the images from each other through a neural network is generated, and the position of the tumor is traced using the discriminator. However, such a method causes processing time to increase and may be difficult to apply to tracing of the position of a tumor which needs to be performed in real time because a plurality of local images are cut out of a transparent image using, for example, raster scanning, and the local images are classified as a tumor or a non-tumor through a discriminator.

CITATION LIST

Patent Literature

[Patent Literature 1]
U.S. Pat. No. 6,819,790

SUMMARY OF INVENTION

Technical Problem

An object of the present invention is to provide a medical image processing device, a medical image processing method, and a program which can rapidly and accurately estimate a target position in a patient from transparent images of the patient in radiation treatment.

Solution to Problem

A medical image processing device of an aspect of the present embodiment includes a first position acquirer, a first converter, a first likelihood image generator, and a learner. The first position acquirer is configured to acquire, as first positions, target positions of a patent in a plurality of first images that are transparent images at a plurality of points in time at which the patient is imaged. The first converter is configured to convert the first positions in the plurality of first images to second positions by expanding movement in a second direction intersecting a first direction in which movement over time of the first positions is large. The first likelihood image generator is configured to generate a first likelihood image showing a distribution of likelihood indicating probability of corresponding to the second positions on the basis of the second positions. The learner is configured to output a model which uses some or all of the plurality of first images and the first likelihood image as training data, and upon receiving part or all of a transparent image, derives a second likelihood image showing a distribution of likelihood indicating probability of the part or all of the transparent image corresponding to the second positions.

Advantageous Effects of Invention

According to the above-described aspect, it is possible to provide a medical image processing device, a medical image processing method, and a program which can automatically trace a tumor in the body of a patient from a transparent image of the patient undergoing radiation treatment.

DESCRIPTION OF EMBODIMENTS

Hereinafter, a medical image processing device, a medical image processing method, and a program of embodiments will be described with reference to the drawings.

First Embodiment

Figure 1:
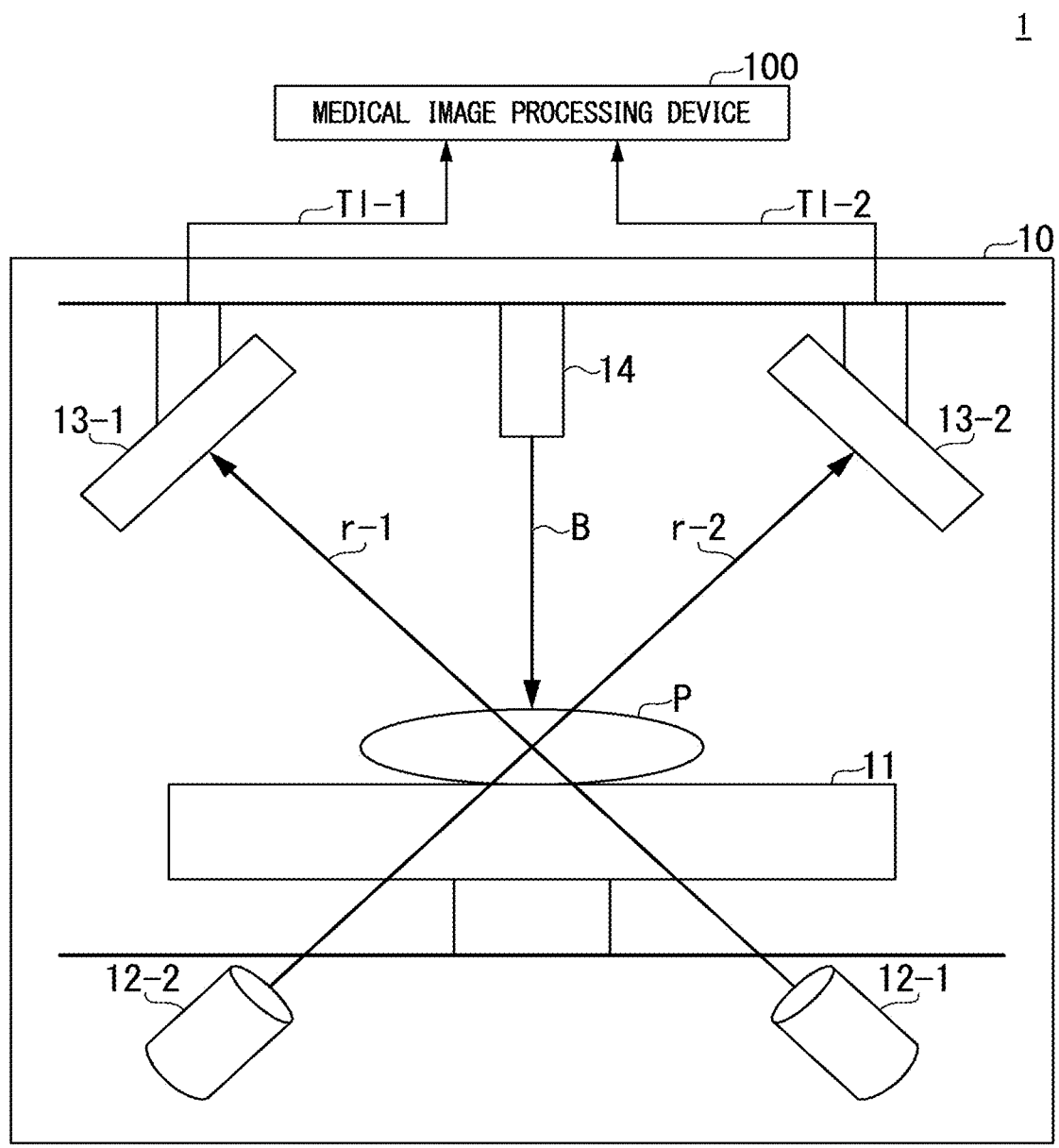
FIG. 1 is a configuration diagram of a treatment system 1 including a medical image processing device 100 of a first embodiment.

FIG. 1 is a configuration diagram of a treatment system 1 including a medical image processing device 100. The treatment system 1 includes, for example, a treatment device 10 and the medical image processing device 100.

The treatment device 10 includes, for example, a bed 11, radiation sources 12-1 and 12-2, detectors 13-1 and 13-2, and a treatment device controller 20. Hereinafter, it is assumed that a hyphen and a numeral subsequent thereto in a reference sign indicate which pair of a radiation source and a detector is used for radiation for transillumination or a transparent image. Description will be given with hyphens and numerals subsequent thereto in signs omitted appropriately.

A patient P receiving treatment is fixed to the bed 11. The radiation source 12-1 applies radiation r-1 to the patient P. The radiation source 12-2 applies radiation r-2 to the patient P at a different angle from that of the radiation source 12-1. The radiation r-1 and r-2 is an example of electromagnetic waves and, for example, is X-rays.

The radiation r-1 is detected by the detector 13-1 and the radiation r-2 is detected by the detector 13-2. The detectors 13-1 and 13-2 are, for example, flat panel detectors (FPDs), image intensifiers, color image intensifiers, or the like. The detector 13-1 detects the energy of the radiation r-1, converts the energy into a digital signal and outputs the digital signal to the medical image processing device 100 as a transparent image TI-1. The detector 13-2 detects the energy of the radiation r-2, converts the energy into a digital signal and outputs the digital signal to the medical image processing device 100 as a transparent image TI-2. Although two pairs of radiation sources and detectors are shown in FIG. 1, the treatment device 10 may include three or more pairs of radiation sources and detectors.

An irradiation gate 14 radiates a treatment beam B to the patient P in a treatment stage. The treatment beam B includes, for example, a heavy particle beam, X-rays, g-rays, an electron beam, a proton beam, a neutron beam, or the like. Although only a single irradiation gate 14 is shown in FIG. 1, the treatment device 10 may include a plurality of irradiation gates.

The transparent image TI may be acquired several days before radiation of the treatment beam B through the irradiation gate 14 or acquired immediately before radiation of the treatment beam B. A user (doctor or the like) of the treatment device 10 sets a treatment plan, for example, using transparent images acquired several days before radiation of the treatment beam B. Treatment planning plans the energy of radiation to be applied to the patient P, an irradiation direction, the shape of an irradiation range, and the like. In a case where radiation of the treatment beam B is performed multiple times, the treatment plan includes a plan of distribution of the dose of the treatment beam B each time. In the treatment plan, the medical image processing device 100 receives designation of an irradiation target position (target position) of the treatment beam B performed by a doctor.

The medical image processing device 100 may derive the position of a marker positioned near a target in the body of the patient P simultaneously with derivation of various types of information about the target. The marker positioned in the body of the patient P is, for example, a metal and has high visibility in the transparent image TI. Accordingly, the marker is traced in a case where the target is difficult to trace.

The medical image processing device 100 designates the position and volume of a tumor, for example, when a boundary between the tumor and a normal region is designated. This volume of the tumor is referred to as a gross tumor volume (GTV), a clinical target volume (CTV), an internal target volume (ITV), a planning target volume (PTV), and the like. The GTV is the volume of a target that can be visually inspected from an image and requires irradiation of the treatment beam B of a sufficient dose in radiation treatment. The CTV is a volume including the GTV and a target having the potential to be treated. The ITV is a volume obtained by adding a predetermined margin to the CTV in consideration of movement of the CTV according to predicted physiological motion of the patient P or the like. The PTV is a volume obtained by adding a margin to the ITV in consideration of an error in position alignment of the patient P to be treated when treatment is performed. The relationship of the following Mathematical expression (1) is established with respect to these volumes.

[Math. 1]

$$GTV \subset CTV \subset ITV \subset PTV \qquad (1)$$

The medical image processing device 100 determines an irradiation field of a treatment beam by adding a margin considering an error likely to be generated during actual treatment set in the treatment plan. The error likely to be generated during actual treatment is, for example, displacement of a patient position in patient positioning, or the like.

Figure 2:
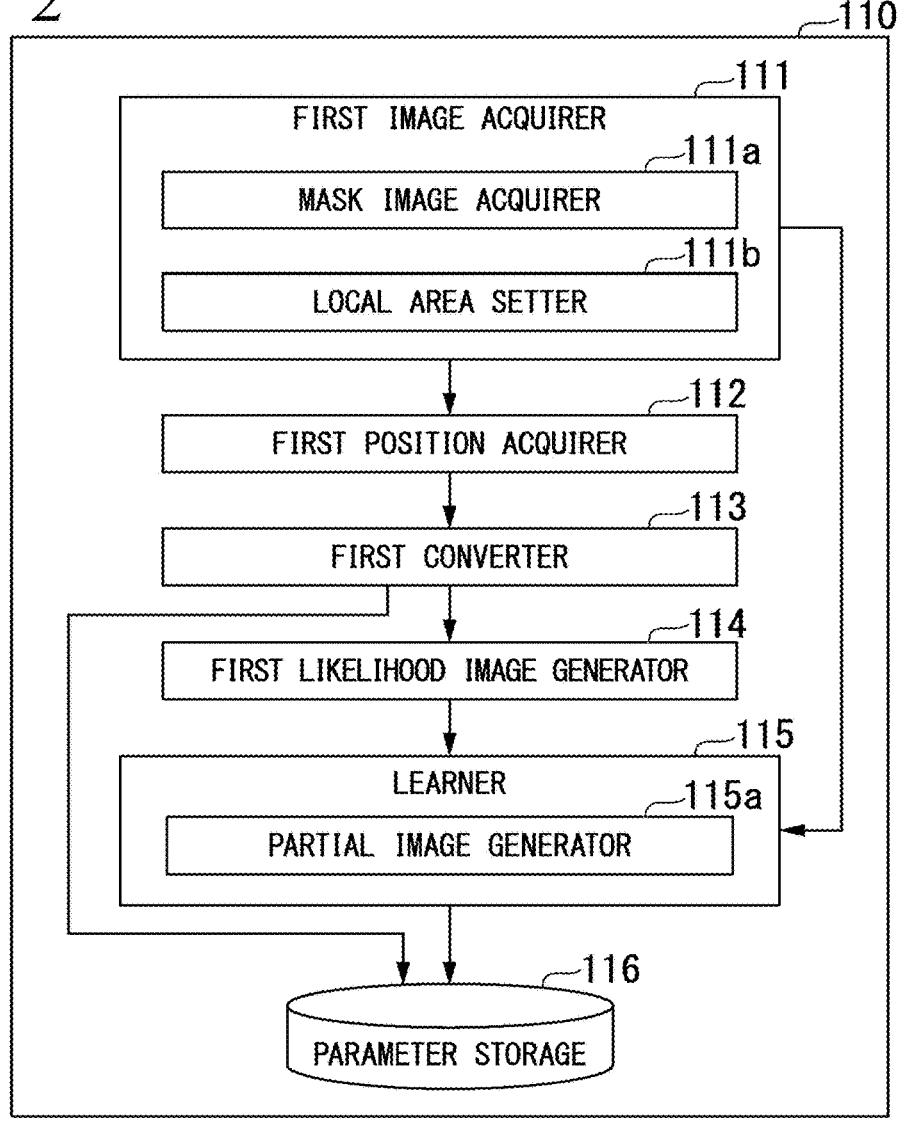
FIG. 2 is a block diagram of a learning device 110 of the first embodiment.

FIG. 2 is a block diagram showing a configuration of a learning device 110 of the first embodiment. The learning device 110 shown in FIG. 2 includes, for example, a first image acquirer 111, a first position acquirer 112, a first converter 113, a first likelihood image generator 114, a learner 115, a parameter storage 116. These components (except the parameter storage 116) are realized, for example, by a hardware processor such as a CPU executing a program (software). Some or all of these components may be realized by hardware (a circuit including circuitry) such as a large scale integration (LSI), an application specific integrated circuit (ASIC), a field-programmable gate array (FPGA), and a graphics processing unit (GPU) or software and hardware in cooperation. The program may be stored in advance in a storage device such as a hard disk drive (HDD) or a flash memory or stored in a detachable storage medium such as a DVD or a CD-ROM and installed in the storage device by setting the storage medium in a drive device.

The first image acquirer 111 first reproduces an imaging device included in the treatment device 10 constituting the treatment system 1. More specifically, in the treatment device 10 constituting the treatment system 1, the positions of the radiation source 12 and the radiation detector 13 are fixed, as shown in FIG. 1. That is, an imaging direction of an imaging device composed of a pair of the radiation source 12 and the radiation detector 13 is fixed in the treatment device 10. Accordingly, when predetermined three-dimensional coordinates are defined in a three-dimensional space in which the radiation source 12 and the radiation detector 13 are installed, the positions of the radiation source 12 and the radiation detector 13 can be represented by coordinate values of three axes. In the following description, information on coordinate values of three axes will be referred to as geometry information of the imaging device composed of the pair of the radiation source 12 and the radiation detector 13.

The first image acquirer 111 acquires a first image before the treatment beam B is radiated to the patient P. The first image is, for example, a DRR image created (reproduced) on the basis of a transparent image such as a three-dimensional CT image captured at the time of treatment planning. Specifically, the first image acquirer 111 creates a DRR image from a transparent image acquired at the time of treatment planning according to geometry information of an imaging device that captures a transparent image TI at the time of treatment. The first image acquirer 111 outputs the acquired first image to the learner 115. The first image acquired by the first image acquirer 111 may be, for example, an X-ray transparent image or the like captured during learning or prior thereto, such as past treatment for the patient P.

The first image acquirer 111 includes, for example, a mask image acquirer 111a and a local area setter 111b. In a case where a subject (e.g., a treatment instrument or a treatment device) other than a tumor that is a main subject is captured in a transparent image TI, the mask image acquirer 111a generates a mask image that covers that region. The mask image acquirer 111a outputs the mask image covering the subject other than the tumor to the local area setter 111b.

The local area setter 111b sets an area in which a part in which the subject other than the tumor is captured is small, that is, an area in which a part in which the tumor is captured is relatively large (e.g., a window area WA (TP) which will be described later), in the mask image output from the mask image acquirer 111a and outputs the set area to the first position acquirer 112 and the learner 115. The local area setter 111b sets an area estimated to have a high learning effect (e.g., a window area WA(k) which will be described later) in the mask image and outputs the set area to the learner 115. The local area setter 111b may receive designation of an area by a doctor or may automatically set an area as will be described below. In the latter case, the local area setter 111b may set the first image and the mask image estimated to have a high learning effect in the learner 115 which will be described later and output them with respect to the window area WA(k). An image estimated to have a high learning effect is, for example, an image having a large luminance value difference.

The first position acquirer 112 acquires information on a target position in the first image output from the first image acquirer 111. The information on the target position is a position at which an affected area of the patient P, that is, a tumor that is an object to which the treatment beam B will be radiated, or the like is present. The information on the target position is information on a position (e.g., a position at which geometry information has been reflected in the center of a tumor which can be confirmed through DRR) identified by a user (e.g., a doctor) of the medical image processing device 100 at the time of treatment planning. The first position acquirer 112 outputs the first image and the information on the target position to the first converter 113. The position identified by the user (e.g., a doctor) of the medical image processing device 100 at the time of treatment planning is an example of a "target position" or a "first position."

The first converter 113 derives a conversion parameter CP and a reverse conversion parameter RCP by performing predetermined conversion processing on the first image on the basis of the information on the target position output from the first position acquirer 112. The first converter 113 associates the target position corresponding to the pixel position of the first image, derived on the basis of the conversion parameter CP, with a pixel position of a first likelihood image and outputs the associated position to the first likelihood image generator 114. The first converter 113 outputs the reverse conversion parameter RCP to the parameter storage 116. The predetermined conversion processing performed on the first image, the conversion parameter CP, and the reverse conversion parameter RCP will be described later.

The first likelihood image generator 114 generates the first likelihood image on the basis of the target position output from the first converter 113 and outputs the first likelihood image to the learner 115. The first likelihood image is, for example, an image in which a likelihood of the target position in the first image (probability of being a position at which a tumor is present) is represented by luminance or the like.

The learner 115 derives a likelihood calculation parameter LP representing a regression learning model of a relationship between some or all first images and the first likelihood image on the basis of some or all first images (more specifically, images of window areas) output from the first image acquirer 111 and the first likelihood image output from the first likelihood image generator 114. The learner 115 outputs the likelihood calculation parameter LP to the parameter storage 116. Some or all first images and the first likelihood image, respiration phases of which are associated with each other, are an example of "training data."

The learner 115 includes, for example, a partial image generator 115a. The partial image generator 115a generates a partial image that is a partial region of the first likelihood image.

Figure 3:
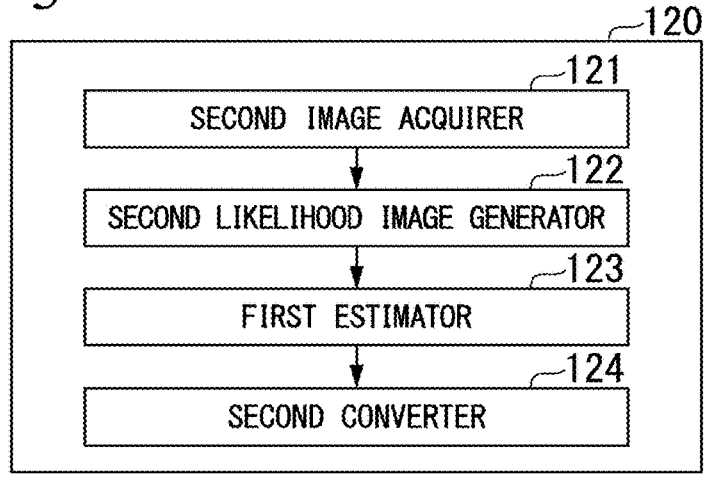
FIG. 3 is a block diagram of a moving object tracking device 120 of the first embodiment.

FIG. 3 is a block diagram showing a configuration of the moving object tracking device 120 of the first embodiment. The moving object tracking device 120 shown in FIG. 3 includes, for example, a second image acquirer 121, a second likelihood image generator 122, a first estimator 123, and a second converter 124. Some or all of these components may be realized by hardware such as an LSI circuit or software and hardware in cooperation like the learning device 110. A program may be stored in advance in a storage device or stored in a detachable storage medium and installed in the storage device by setting the storage medium in a drive device.

The second image acquirer 121 acquires second images that are transparent images TI captured at predetermined time intervals immediately before or during radiation of the treatment beam B to the patient P. The second image acquirer 121 outputs the second images to the second likelihood image generator 122.

The second image acquirer 121 obtains a target position as a projection matrix. Accordingly, the second image acquirer 121 obtains a projection matrix associated with each imaging device from geometry information in advance. That is, the second image acquirer 121 obtains a projection matrix for each imaging device. In addition, the second image acquirer 121 calculates coordinate values of three-dimensional coordinates indicating a target position within a predetermined three-dimensional space from target positions captured in two first images using the principle of triangulation. Accordingly, the second image acquirer 121 calculates the position where the target position within the predetermined three-dimensional space has been captured in the transparent image TI of the patient P.

The second likelihood image generator 122 generates a second likelihood image on the basis of the second images output from the second image acquirer 121. The second likelihood image generator 122 generates the second likelihood image associated with the second images, for example, on the basis of the likelihood calculation parameter LP output from the parameter storage 116. The second likelihood image generator 122 outputs the generated second likelihood image to the first estimator 123.

The first estimator 123 estimates a target position in the second images on the basis of the second likelihood image and the second images output from the second likelihood image generator 122. The first estimator 123 outputs the estimated target position to the second converter 124.

The second converter 124 derives a target position (i.e., a position to which the treatment beam B is radiated) on the basis of the estimated target position output from the first estimator 123. For example, the second converter 124 derives the target position by converting the estimated target position output from the first estimator 123 using the reverse conversion parameter RCP output from the parameter storage 116. Conversion processing performed by the second converter 124 is processing of performing conversion in a direction reverse to conversion processing performed by the first converter 113.

Figure 4:
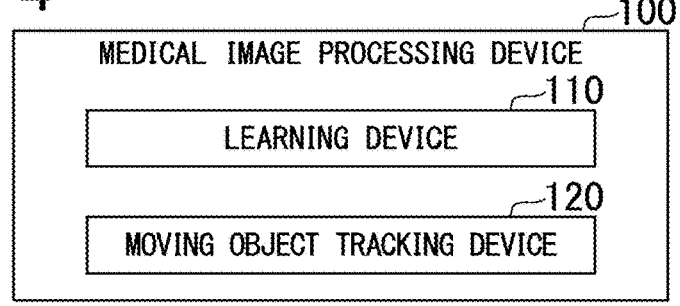
FIG. 4 is a block diagram of the medical image processing device 100 of the first embodiment.

FIG. 4 is a block diagram showing a configuration of the medical image processing device 100 of the first embodiment. The medical image processing device 100 shown in FIG. 4 includes, for example, the learning device 110 and the moving object tracking device 120.

Predetermined conversion processing of first images performed by the first converter 113, a method of deriving the conversion parameter CP and the reverse conversion parameter RCP, and a method of using the same will be described using FIGS. 5 to 7.

Figure 5:
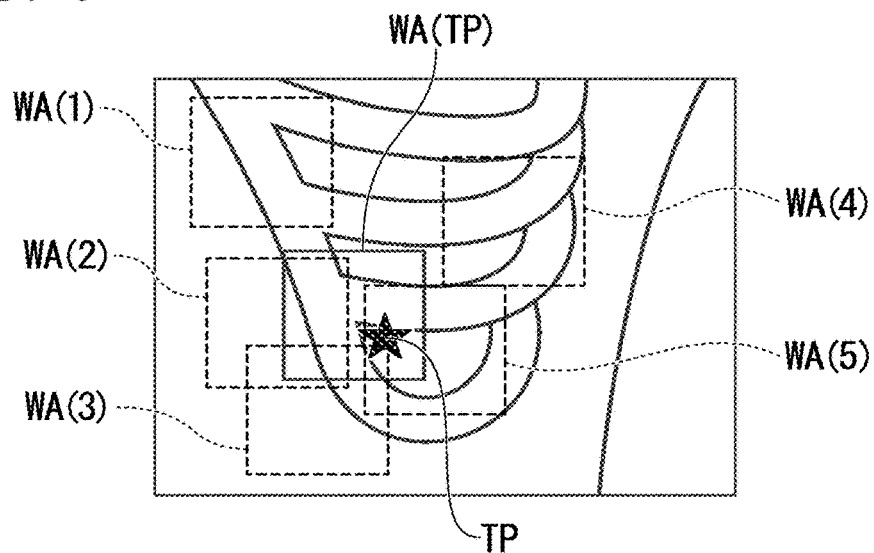
FIG. 5 is a diagram showing an example of a state in which a first converter 113 processes a transparent image TI.

FIG. 5 is a diagram showing an example of a state of image analysis performed by the first image acquirer 111 for transparent images TI. The transparent image TI of FIG. 5 shows that a target position TP to which the treatment beam B is radiated is present in the thoracoabdominal part.

The first image acquirer 111 sets a plurality of window areas WA shown in FIG. 5 for the transparent images TI of a plurality of points in time. The window areas WA are set, for example, such that they include images of positions at which characteristic parts of the transparent images TI are extracted. The characteristic parts of the transparent images TI are, for example, clearly appearing parts such as a tumor, a marker, a diaphragm, and the like. In the following description, there are cases in which a window area including a target position TP in an image area and represented by a solid line associated with the first likelihood image is referred to as a window area WA(TP) and a window area represented by a broken line that is not associated with the first likelihood image is referred to as a window area WA(k) (k is an integer). In the example of FIG. 5, k is an integer in the range of 1 to 5. Positions at which the window areas WA occupy the first image are fixed.

The local area setter 111b sets the window area WA(TP) such that it includes all trajectories of corrected target positions TP-1 to TP-6. When the window areas WA are automatically set, the local area setter 111b sets a local area having a large luminance difference of the first images associated with TP-1 to TP-6 as a window area WA(k). Alternatively, the local area setter 111b may set a local area having a long optical flow trajectory as a window area WA(k). Alternatively, the local area setter 111b may set a local area including many feature points acquired through image corner detection or the like as a window area WA(k). In a case where an affected part is positioned at the lungs, for example, an image pattern of the target captured in the transparent image TI is clear and thus the local area setter 111b may preferentially set a window area WA(k) including that position. In a case where an affected part is in a large organ such as the liver, the target position appearing in the transparent image TI is likely to be unclear. In such a case, the local area setter 111b sets a clearly appearing part such as the boundary of the diaphragm as a window area WA(k).

Figure 6:
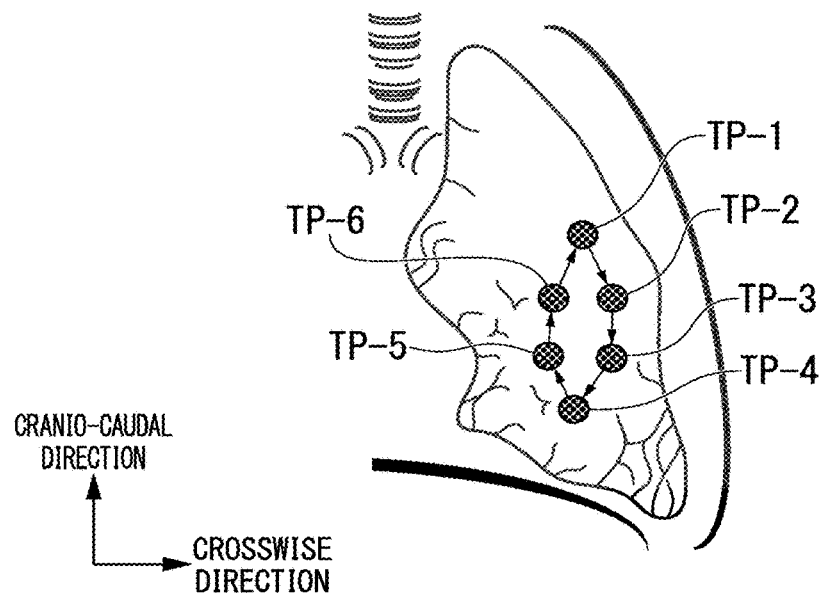
FIG. 6 is a diagram showing an example of a trajectory of a target position TP.
Figure 7:
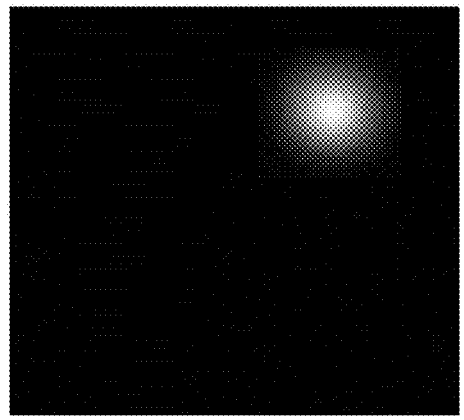
FIG. 7 is a diagram showing an example of a first likelihood image generated by the medical image processing device 100.

FIG. 6 is a diagram showing an example of characteristics of movement of a target position TP in a window area WA(TP) of a plurality of points in time. Hereinafter, it is assumed that a hyphen and a numeral subsequent thereto in a reference sign indicate a target position (respiration phase). There are cases in which description is given with hyphens and numerals subsequent thereto in signs omitted appropriately. The target position TP moves according to respiration of the patient P, for example. The target position TP moves, for example, in the order of target positions TP-1 to TP-6 according to respiration of the patient P, as shown in FIG. 6. Accordingly, the target position TP tends to significantly move in a cranio-caudal direction of the patient P in which the diaphragm considerably moves. On the other hand, the target position TP moves less in a crosswise direction (any direction on a plane having a front-back direction and a left-right direction as axes) that intersects the cranio-caudal direction shown in FIG. 6. That is, in a case where imaging is performed with the cranio-caudal direction aligned with the vertical direction of a transparent image TI, when the target position TP is projected to the transparent image TI, movement of the target position TP in the horizontal direction of the transparent image decreases. That is, learning performed by the learner 115 may become difficult because a change in the horizontal direction of the first likelihood image generated on the basis of the target position TP is insignificant. Accordingly, the first converter 113 derives the conversion parameter CP for improving the learning effect of the learner 115.

Hereinafter, the conversion parameter CP will be described. The conversion parameter CP includes parameter A and b that establish the following linear transformation y=Ax+b in order to associate a target position in a first image with a target position in the first likelihood image. Here, x=($u_t$, $v_t$) and y=($u_t'$, $v_t'$) respectively indicate image coordinates of the first image and the first likelihood image. A is a 2×2 matrix. b is an offset. For example, in a case where A is a unit matrix, each pixel position of the first image corresponds to a pixel position in the first likelihood image. Further, in a case where the image size of the first image is greater than the first likelihood image, the first converter 113 associates pixels of a partial area of the first image with each pixel of the first likelihood image.

As another example, decimal pixels of the first image may correspond to a pixel position with integer accuracy of the first likelihood image. That is, in a case where all diagonal elements of A are a ½ diagonal matrix and b is a zero vector, a pixel of a pixel position (x/2, y/2) of the first image is associated with (x, y) of the first likelihood image.

The aforementioned problem is caused by insignificant change in the target position TP in the first likelihood image because association is performed by the same scale as that in a case where A is a unit matrix. Accordingly, A is adjusted such that a pixel position with decimal accuracy of the first image is associated with a pixel position with integer accuracy of the first likelihood image. Accordingly, the learning effect of the learner 115 is improved by applying change in the horizontal direction of the first likelihood image. In a case where the trajectory of movement of the first position in the first image is an oval trajectory, for example, the matrix A is adjusted such that the trajectory becomes an accurate circle on the first likelihood image. This matrix A is an example of a "transformation matrix determined on the basis of movement over time of a first position." The reverse conversion parameter RCP is a reverse conversion parameter of the aforementioned linear transformation. Specifically, the reverse conversion parameter RCP is an inverse matrix of the matrix A and the offset b.

A target position in the first image which has been corrected through the aforementioned linear transformation is referred to as a corrected target position TP #. The corrected target position TP # is an example of a "second position." The cranio-caudal direction of the patient P shown in FIG. 6 is an example of a "first direction" and the crosswise direction is an example of a "second direction" perpendicular to the first direction.

Hereinafter, processing through which the first likelihood image generator 114 generates the first likelihood image will be described. FIG. 7 is an example of the first likelihood image generated by the first likelihood image generator 114. A part (white part) with high luminance in FIG. 7 is a part in which a target position is highly likely to be present. The first likelihood image of FIG. 7 is supposed to have a target position present in a right top part of the image. The first likelihood image generator 114 generates the first likelihood image on the basis of a second position output from the first converter 113, for example. The first likelihood image generator 114 derives a likelihood image L(u, v) according to Mathematical expression (2) below in a case where the coordinates indicating the second position are ($u_t'$, $v_t'$).

[Math. 2]

$$L(u, v) = \exp\left(-\frac{(u - u_t')^2 + (v - v_t')^2}{2\sigma^2}\right) \quad (2)$$

σ in Mathematical expression (2) is an arbitrary parameter set by a user. For example, σ is set as a higher value when resolution per pixel is higher. Although the image size of the first likelihood image generated by the first likelihood image generator 114 may be arbitrarily set, it may be set the image size such that the trajectory of a target position is within the first likelihood image, as described above. Accordingly, the image size of the first likelihood image can be reduced as compared to the first image.

Hereinafter, processing through which the learner 115 derives the likelihood calculation parameter LP will be described. For example, the learner 115 uses images cut off from one or a plurality of window areas WA(k) in the first image and the first likelihood image as learning data and generates a model that derives the first likelihood image when an image of the window areas WA(k) is input.

The learner 115 obtains, for example, a function f in a case where a mathematical expression representing a relationship between a vector x that connects the images cut off from one or the plurality of window areas WA(k) in the first image and a vector y of the first likelihood image is Mathematical expression (3) below. The learner 115 derives the function f using a vector in which pixel values of the first image are arranged as x and using a vector in which pixel values of the first likelihood image are arranged as y.

[Math. 3]

$$y=f(x) \quad (3)$$

The learner 115 derives the function f by which an error Δ=y−f(x) decreases using the vector y of the first likelihood image output from the first likelihood image generator 114. The learner 115 may derive the function f using a deep neural network or using other machine learning methods such as a neural network, a convolutional neural network, and a decision tree. In a case where functions f of a plurality of patterns are derived using a predetermined number of the plurality of patterns, for example, the learner 115 may learn all of the functions f of the plurality of patterns.

Figure 8:
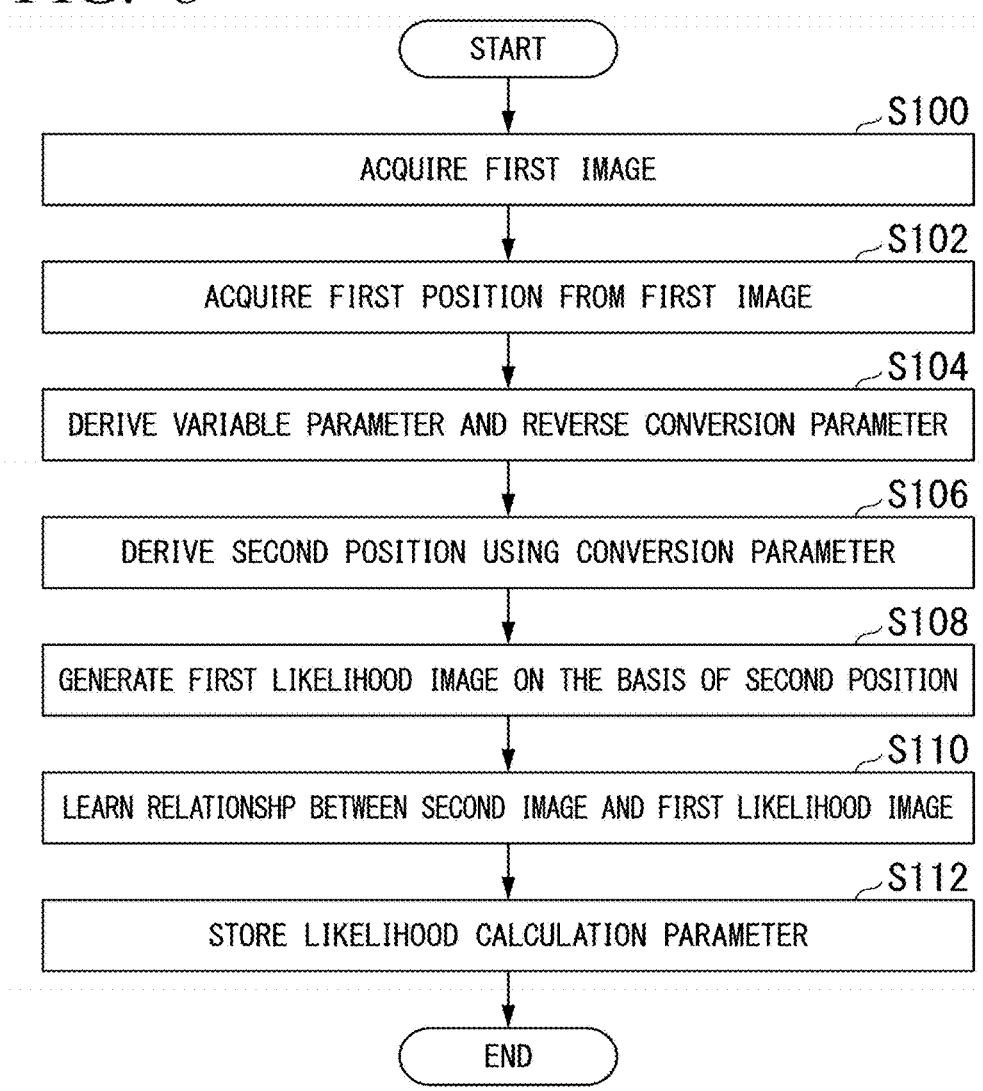
FIG. 8 is a flowchart showing an example of a processing flow of the learning device 110.

FIG. 8 is a flowchart showing an example of a processing flow of the learning device 110. First, the first image acquirer 111 acquires first images of a plurality of points in time (step S100). Next, the first position acquirer 112 acquires first positions associated with the acquired first images of the plurality of points in time (step S102). Next, the first converter 113 derives the conversion parameter CP and the reverse conversion parameter RCP on the basis of the trajectory of the acquired first positions of the plurality of points in time and causes the parameter storage 116 to store the conversion parameter CP and the reverse conversion parameter RCP (step S104). Next, the first converter 113 derives second positions by converting the first positions on the basis of the conversion parameter CP (step S106). Next, the first likelihood image generator 114 creates a first likelihood image on the basis of the second positions (step S108). Next, the learner 115 learns a relationship between second images and the first likelihood image using the second images and the first likelihood image (step S110). Next, the learner 115 causes the parameter storage 116 to store the likelihood calculation parameter LP (step S112). Hereby, processing of this flowchart ends.

Next, processing through which the second likelihood image generator 122 of the moving object tracking device 120 generates a second likelihood image associated with a second image will be described. The second likelihood image generator 122 generates a second likelihood image associated with a second image using the aforementioned Mathematical expression (3) on the basis of the second image output from the second image acquirer 121 and the likelihood calculation parameter LP acquired from the parameter storage 116. The second likelihood image generator 122 uses partial images of the second image at the same positions as those in the window areas WA(k) set by the local area setter 111b as input of the aforementioned Mathematical expression (3). Here, association of pixel positions of the output second likelihood image and the second image is the same as association of the first likelihood image and the first image.

Hereinafter, a method for estimating a second position in a second image by the first estimator 123 will be described. For example, the first estimator 123 estimates a pixel position at which likelihood is maximized in a second likelihood image output from the second likelihood image generator 122 as a second position. The first estimator 123 may derive a pixel position from a weight average of each pixel position which uses a likelihood indicated by the second likelihood image output from the second likelihood image generator 122 as a weight and use the derived pixel position as the second position. In this case, the first estimator 123 may perform weight averaging such that weights decrease as any of a tumor position and a trajectory thereof obtained at the time of treatment planning or in past treatment increases. In a case where a target position can be acquired from a second image initially acquired by the second image acquirer 121, the first estimator 123 predicts the second position in the second image to be acquired next time and after the next time on the basis of the target position. A plurality of predicted position candidates may be prepared and a position for which weights have been averaged using likelihoods of the second likelihood image associated with the positions as weights may be used as the second position. Predicted position candidates may be prepared through a method such as a particle filter.

When the estimated target position is three-dimensional coordinates, the first estimator 123 may acquire likelihood from the second likelihood image at positions obtained by projecting the predicted position to respective images (transparent images TI-1 and TI-2) and use the product thereof as a likelihood of the estimated target position. When the predicted position is two-dimensional coordinates, likelihood for target positions in two images for which epipolar constraint is established may be derived.

Hereinafter, processing through which the second converter 124 converts a target position using the reverse conversion parameter RCP will be described. The second converter 124 converts the target position to a target position x in the second image represented by Mathematical expression (4) below according to the estimated target position y=(u', v') in the second likelihood image output from the first estimator 123 and the reverse conversion parameter RCP ($A^{-1}$, b) acquired from the parameter storage 116.

[Math. 4]

$$x=(\tilde{u},\tilde{v}) \qquad (4)$$

That is, the second converter 124 calculates $x=A^{-1}y-b$. The second converter 124 may output a position obtained by correcting the converted target position using a model of the trajectory of the second position created in the treatment planning stage. The second converter 124 models a relationship $u_t=r(v_t)$ (r is a function, for example) between $u_t$ and $v_t$ on the basis of $(u_t, v_t)$ that is a position in a first image of a tumor acquired from the first position acquirer 112. The model is a linear regression model that can be represented by a mathematical expression such as $u_t=av_t+b$ (a and b are arbitrary values), for example. The second converter 124 may substitute the output value as represented by Mathematical expression (5) below using the derived model.

[Math. 5]

$$\tilde{u}_t \leftarrow r(\tilde{v}_t) \qquad (5)$$

Second images acquired by the second image acquirer 121 are two images (transparent images TI-1 and TI-2) simultaneously captured in different directions in the treatment device 10 shown in FIG. 1, for example. That is, the second image acquirer 121 can acquire the second position associated with each image. Accordingly, the second image acquirer 121 may obtain the second position in a three-dimensional space for which epipolar constraint is established from each of the transparent images TI-1 and TI-2. The epipolar constraint is a geometric constraint based on the fact that a relative position relationship between two imaging devices is known and represents a constraint that a center point of the same subject captured in one image is constrained on an epipolar line on another image. However, since the second position associated with each image is not limited to conforming to the epipolar constraint, the second image acquirer 121 derives the second position in the three-dimensional space using a least squares method.

Figure 9:
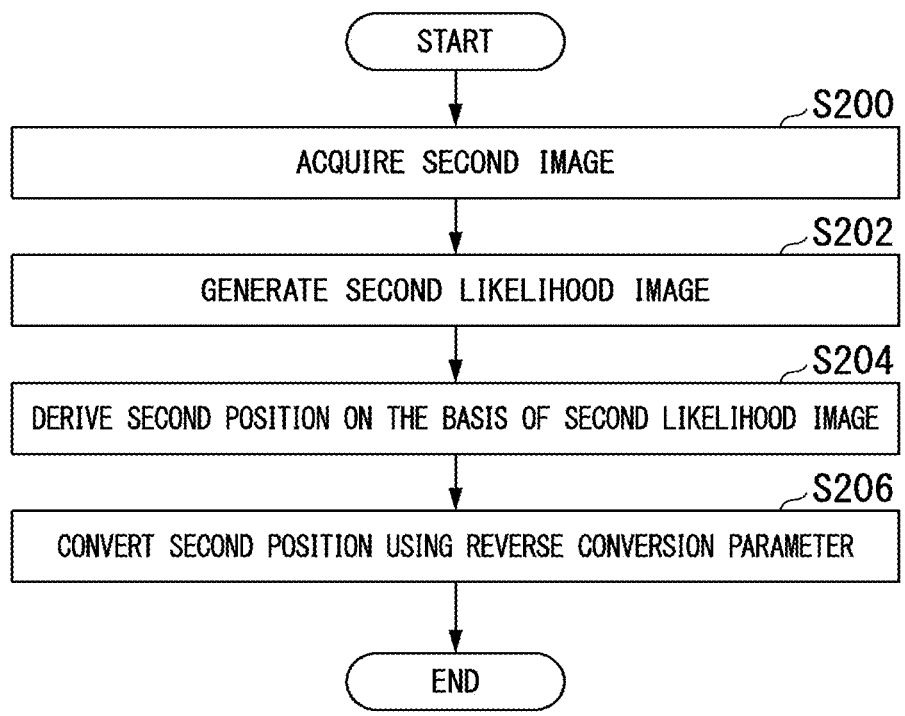
FIG. 9 is a flowchart showing an example of a processing flow of the moving object tracking device 120.

FIG. 9 is a flowchart showing an example of a processing flow of the moving object tracking device 120. The flowchart shown in FIG. 9 is performed, for example, after processing of the flowchart shown in FIG. 8.

First, the second image acquirer 121 acquires a second image (step S200). Next, the second likelihood image generator 122 generates a second likelihood image (step S202). Next, the first estimator 123 derives a second position on the basis of the second likelihood image (step S204). Next, the second converter 124 converts the second position according to a reverse conversion parameter and derives a target position (step S206). Hereby, processing of this flowchart ends.

As described above, in the medical image processing device 100 of the first embodiment, a target position can be rapidly traced with high accuracy from a transparent image TI of the patient P under radiation in radiation treatment according to the learning device 110 which learns a target position derived at the time of treatment planning and derives the conversion parameter CP and the reverse conversion parameter RCP used when a target position in the transparent image TI is derived, and the likelihood calculation parameter LP used to derive a likelihood in the transparent image, and the moving object tracking device 120 which performs derivation of a target position using a likelihood in the transparent image TI acquired when the treatment beam B is radiated using the transparent image TI acquired when the treatment beam B is radiated and the various parameters derived by the learning device 110.

Second Embodiment

Hereinafter, a second embodiment will be described. A medical image processing device 100A of the second embodiment will be described. In the following description, parts having the same functions as those described in the first embodiment will be denoted by the same names and signs and detailed description of the functions thereof will be omitted.

Figure 10:
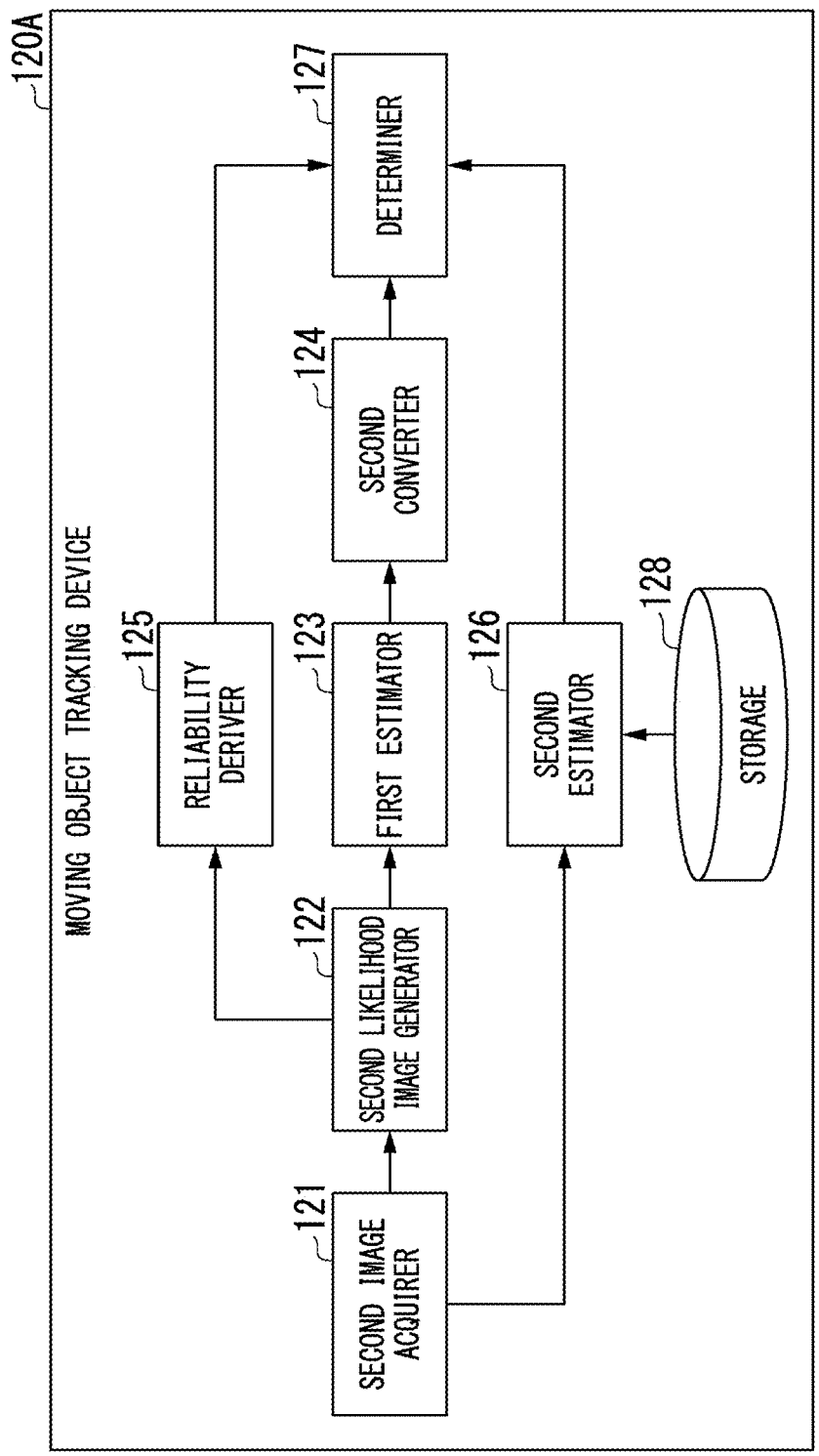
FIG. 10 is a block diagram of a moving object tracking device 120A of a second embodiment.

FIG. 10 is a block diagram showing a configuration of a moving object tracking device 120A. The moving object tracking device 120A of FIG. 10 differs from the moving object tracking device 120 of the first embodiment shown in FIG. 3 in that the former includes a reliability deriver 125, a second estimator 126, a determiner 127, and a storage 128. Accordingly, the following description will focus on the reliability deriver 125, the second estimator 126, the determiner 127, and the storage 128.

The reliability deriver 125 derives reliability on the basis of the second likelihood image output from the second likelihood image generator 122. The reliability is a degree of evaluating reliability of the second likelihood image generated by the second likelihood image generator 122. The reliability deriver 125 outputs the derived reliability to the determiner 127.

The second estimator 126 estimates a target position from a second image output from the second image acquirer 121 and outputs the estimation result to the determiner 127. The second estimator 126 is, for example, a template matching unit which performs matching processing on the second image using a transparent image TI acquired at the time of treatment planning or the like or an image area including a target position of the second image acquired before radiation of the treatment beam B as a template image. The second estimator 126 regards a level of a matching degree (or correlation degree) with the template image as a likelihood, for example, and derives two-dimensional coordinates or three-dimensional coordinates of the target position like the first estimator 123. Here, the matching degree is obtained by normalized cross-correlation, for example. The second estimator 126 causes the storage 128 to store the template image used when template matching is performed.

The determiner 127 determines which one of the target position output from the second converter 124 and the estimated target position output from the second estimator 126 will be a target position of the treatment beam B. The determiner 127 determines a target position, for example, on the basis of the reliability output from the reliability deriver 125. The determiner 127 determines that the target position output from the second converter 124 is employed in a case where the reliability is equal to or greater than a threshold value set in advance, for example. The determiner 127 determines that the estimated target position output from the second estimator 126 is employed in a case where the reliability is less than the threshold value set in advance. The determiner 127 is an example of a "third estimator." The target position determined to be employed by the determiner 127 is an example of a "third position."

Hereinafter, reliability derivation processing of the reliability deriver 125 will be described. The reliability deriver 125 calculates reliability, for example, using the function f derived by the learner 115. The reliability deriver 125 derives high reliability in a case where a second image is a transparent image TI similar to a first image when the function f has been derived. The reliability deriver 125 derives low reliability in a case where the second image is a transparent image TI in a different pattern from the first image when the function f has been derived. This case may be a case in which depth of respiration of the patient P is different when the first image is captured and when the second image is captured.

Figure 11:
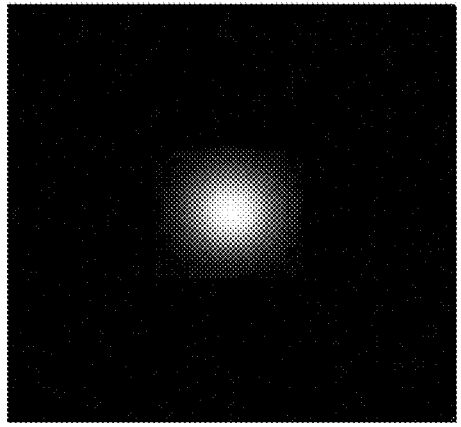
FIG. 11 is a diagram showing an example of a second likelihood image generated by the moving object tracking device 120A.
Figure 12:
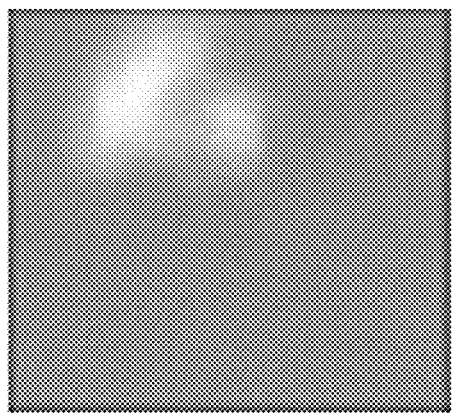
FIG. 12 is a diagram showing another example of the second likelihood image generated by the moving object tracking device 120A.

A difference between likelihood images in a case in which the reliability derived by the reliability deriver 125 is high and a case in which the derived reliability is low will be described using FIG. 11 and FIG. 12. FIG. 11 is an example of the second likelihood image generated by the moving object tracking device 120A of the second embodiment. The reliability deriver 125 derives high reliability with respect to a likelihood image having a large luminance difference (brightness difference) between an area having highest luminance and an area having lowest luminance, as shown in FIG. 11. The reliability deriver 125 derives high reliability in a case where the outline of the area having highest luminance is relatively clear, as shown in FIG. 11, and a case where the shape of an area having luminance of a specific value or more is a round shape. FIG. 12 is another example of the second likelihood image generated by the moving object tracking device 120A of the second embodiment. The reliability deriver 125 derives low reliability with respect to a likelihood image having a relatively small luminance difference (brightness difference) between an area having highest luminance and an area having lowest luminance, as shown in FIG. 12. The reliability deriver 125 derives low reliability in a case where the outline of the area having highest luminance is obscure, as shown in FIG. 12, and a case where the shape of an area having luminance of a specific value or more is not a round shape.

Figure 13:
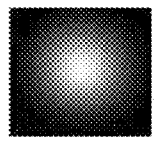
FIG. 13 is a diagram showing an example of an artificial image patch generated by a medical image processing device 100A.

The first likelihood image generator 114 artificially creates a likelihood image patch having high reliability, as shown in FIG. 13, using Mathematical expression (2). Accordingly, a trained image acquired by a likelihood calculation unit 118 is also highly likely to be an image close to FIG. 11, but the likelihood image having low reliability as shown in FIG. 12 may be likely to be output. Accordingly, the reliability deriver 125 derives, for example, a correlation value of the second likelihood image output from the second likelihood image generator 122 and the artificially created likelihood image patch as reliability.

The reliability deriver 125 scans an artificial image patch generated through the same method as that used by the first likelihood image generator 114 shown in FIG. 13 in the second likelihood image output from the second likelihood image generator 122, for example, to calculate correlation values of respective positions and derives a maximum value or an average value of the calculated correlation values as reliability. The reliability deriver 125 may limit a range in which the artificial image patch is scanned to a position converted by the second converter 124 from a position at which likelihood is maximized in the second likelihood image output from the second likelihood image generator 122 or to surroundings including the position.

In a case where reliability is lower than a predetermined value, for example, the determiner 127 causes an output device such as a display of the treatment system 1 to display a warning message to a user. Further, if the treatment beam B is being radiated, the determiner 127 may output a command for stopping irradiation to the treatment system 1 or the radiation source 12. The determiner 127 acquires the target position output from the second converter 124, the reliability output from the reliability deriver 125, and the estimated target position from the second estimator 126 and outputs a target position determined using them. The determiner 127 determines the target position, for example, according to Mathematical expression (6) or Mathematical expression (7). Here, α and $\alpha_1$ represent reliability, $z_1$ represents position 1 derived by the second converter 124, $z_2$ represents position 2 derived by the second estimator 126, and $\alpha_2$ represents a correlation value with respect to the scanned artificial image patch.

[Math. 6]

$$\begin{cases} z = \alpha z_1 + (1-a)z_2 & (6) \\ z = \dfrac{\alpha_1}{a_1+\alpha_2}z_1 + \dfrac{\alpha_2}{a_1+\alpha_2}z_2 & (7) \end{cases}$$

Figure 14:
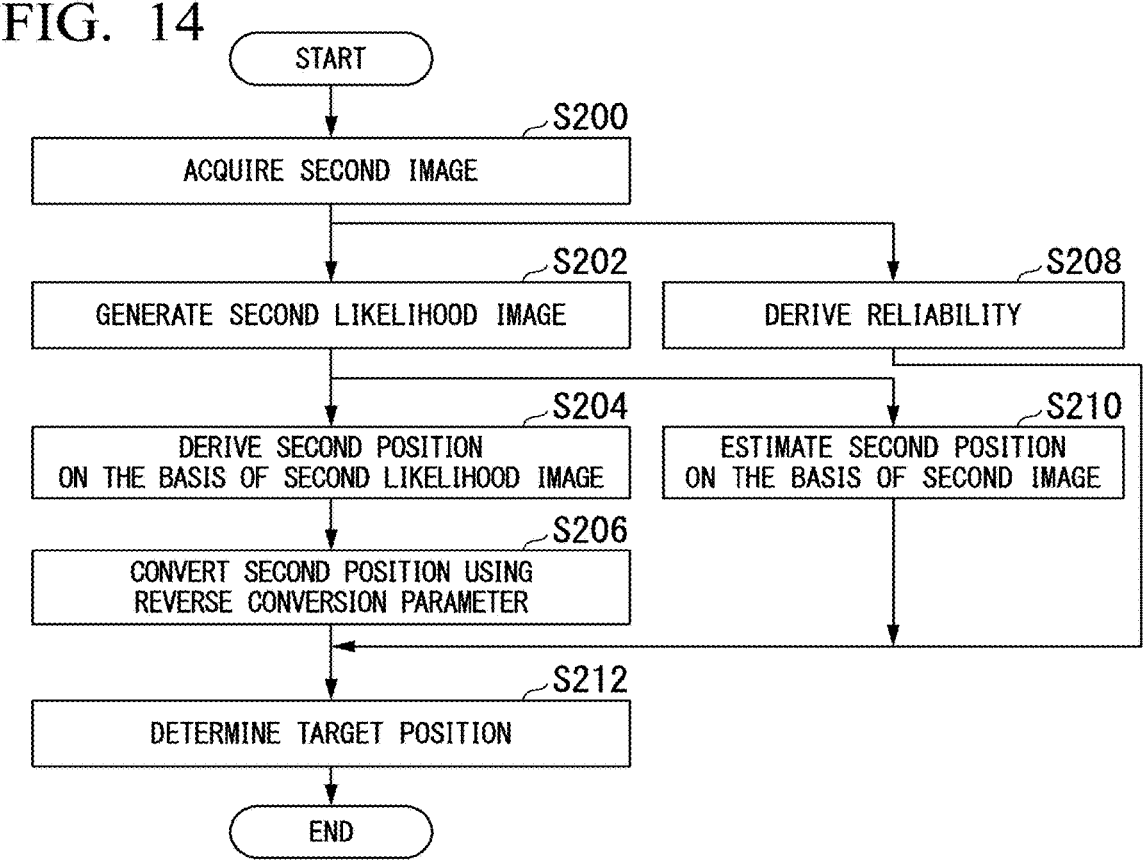
FIG. 14 is a flowchart showing an example of a processing flow of the moving object tracking device 120A.

FIG. 14 is a flowchart showing an example of a processing flow of the moving object tracking device 120A of the medical image processing device 100A. Description of step S200 to step S206 the same as those of the processing flow shown in FIG. 9 will be omitted.

The reliability deriver 125 derives reliability on the basis of the second likelihood image after processing of step S202 (step S208). The second estimator 126 estimates a second position on the basis of the second image after processing of step S200 (step S210). The determiner 127 determines a target position from the processing results of step S206, step S208 and step S210 (step S212). Hereby, processing of this flowchart ends.

As described above, the medical image processing device 100A of the second embodiment can derive reliability of the second likelihood image output from the second likelihood image generator 122 and determine a target position on the basis of the reliability or stop the determination even when the second likelihood image generated by the second likelihood image generator 122 of the moving object tracking device 120A is not a desired result in a case where a transparent image pattern that does not appear in the first image in the learning device 110 appears when the second image is captured, that is, realize robustness (robust stability), in addition to acquisition of the same effect as the medical image processing device 100 of the first embodiment.

Third Embodiment

Hereinafter, a third embodiment will be described. A moving object tracking device 120B of the third embodiment will be described.

Figure 15:
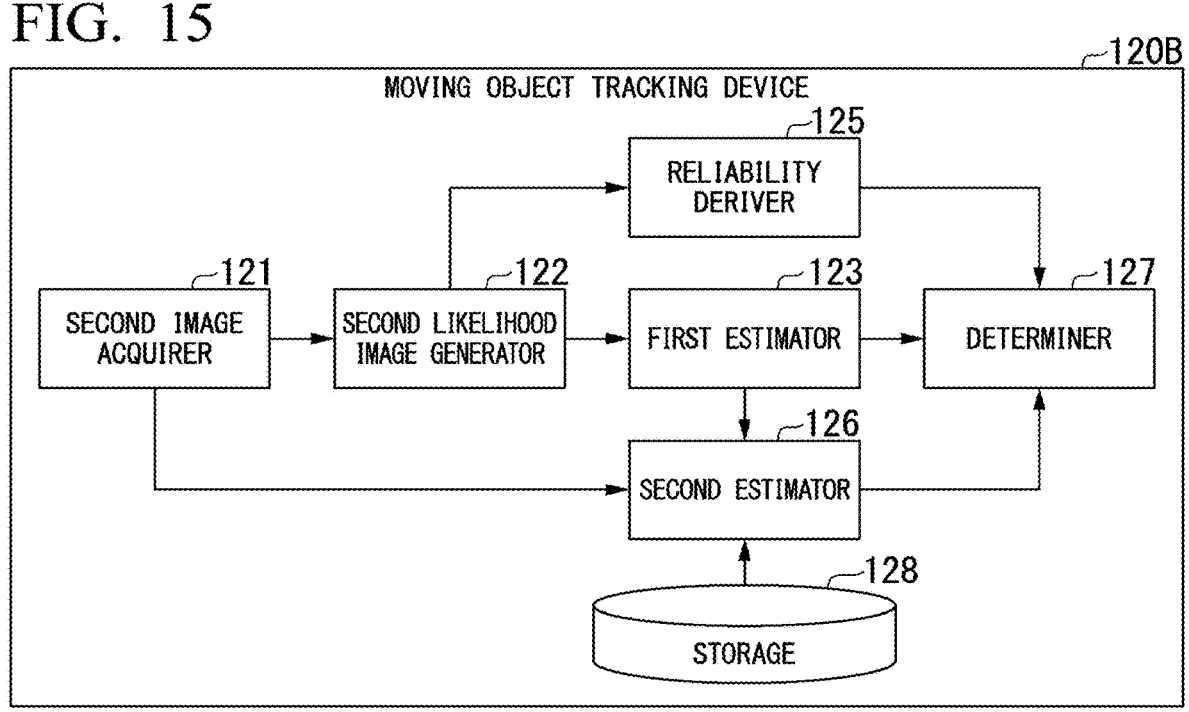
FIG. 15 is a block diagram of a moving object tracking device 120B of a third embodiment.

FIG. 15 is a block diagram showing a configuration of the moving object tracking device 120B of the third embodiment. The following description will focus on differences between the moving object tracking device 120A of the second embodiment and the moving object tracking device 120B of the third embodiment.

The second estimator 126 of the moving object tracking device 120B estimates a target position in a second image on the basis of the second image output from the second image acquirer 121 and the reliability output from the reliability deriver 125, updates an estimation parameter necessary to estimate the target position in the second estimator 126, and outputs an estimation result to the determiner 127. Since there is change over time in the body of the patient P in general, it is desirable that a template image used in the second estimator 126 be updated to an image in which a newest state has been reflected. Accordingly, the moving object tracking device 120B causes the storage 128 to store a partial image associated with high reliability derived by the reliability deriver 125 as a template image.

Figure 16:
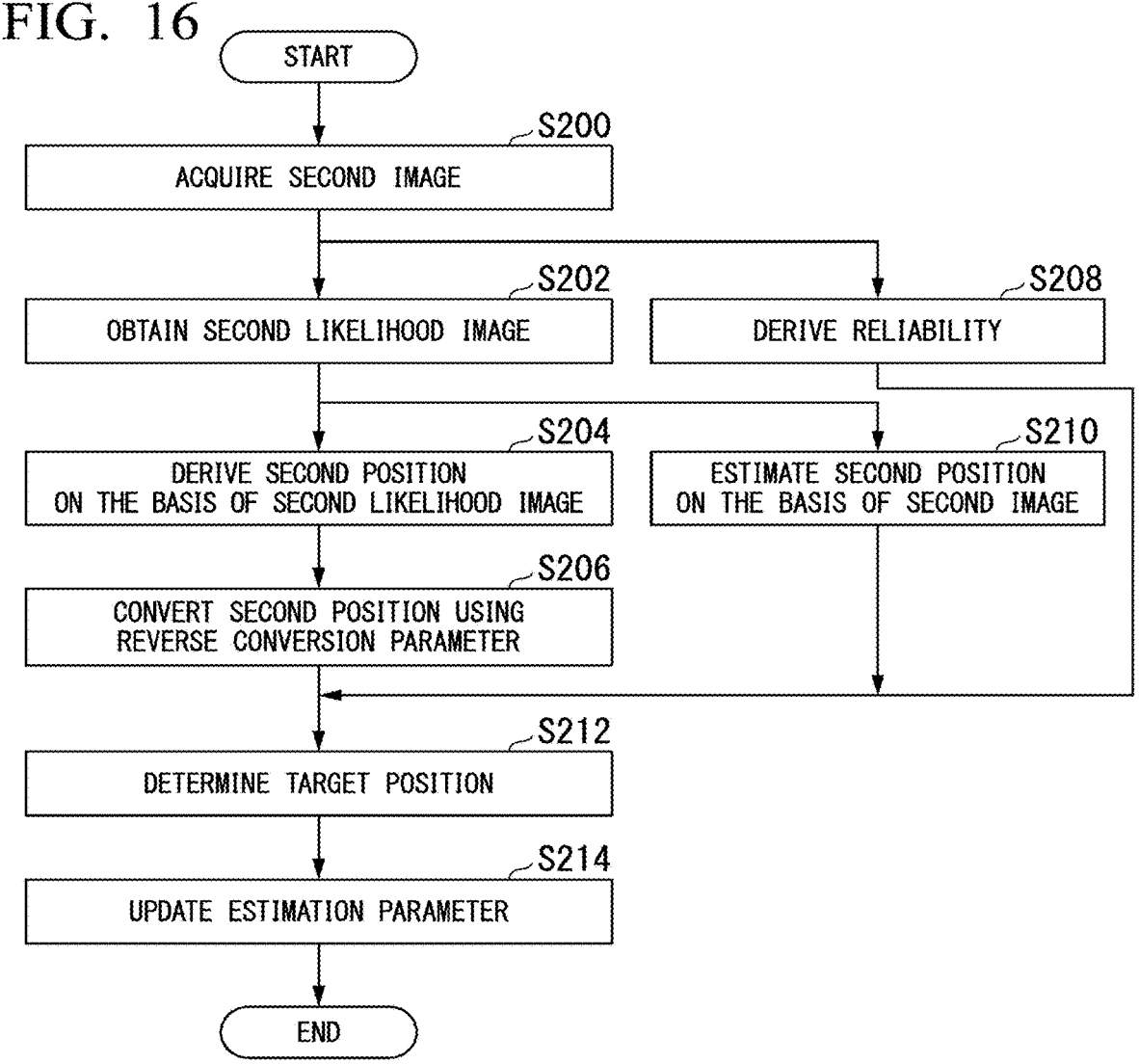
FIG. 16 is a flowchart showing an example of a processing flow of the moving object tracking device 120B.

FIG. 16 is a flowchart showing an example of a processing flow of the moving object tracking device 120B of the medical image processing device 100B. Description of steps the same as those of processing flows shown in FIG. 9 and FIG. 14 will be omitted.

After processing of step S212, the second estimator 126 derives and stores an estimation parameter (step S214). Hereby, processing of this flowchart ends.

As described above, the medical image processing device 100B of the third embodiment can update a template image to a template image having high reliability to determine a target position by reflecting a newest state of an affected part of the patient P in addition to acquisition of the same effect as that of the medical image processing device 100A of the second embodiment.

According to at least one of the above-described embodiments, it is possible to rapidly trace a target position with high accuracy from a transparent image TI of the patient P under radiation in radiation treatment by including the learning device 110 which learns a target position derived at the time of treatment planning and derives the conversion parameter CP and the reverse conversion parameter RCP used when a target position in the transparent image TI is derived, and the likelihood calculation parameter LP used to derive a likelihood in the transparent image, and the moving object tracking device 120 which performs derivation of a target position using a likelihood in the transparent image TI acquired when the treatment beam B is radiated using the transparent image TI acquired when the treatment beam B is radiated and the various parameters derived by the learning device 110.

Although several embodiments of the present invention have been described, these embodiments have been suggested as examples and are not intended to limit the scope of the invention. These embodiments can be implemented in other various forms and various omissions, substitutions and modifications are possible without departing from essential characteristics of the invention. These embodiments and modifications thereof are included in the scope and essential characteristics of the invention and also included in the invention disclosed in the attached claims and the equivalents thereof.

INDUSTRIAL APPLICABILITY

According to the above-described embodiments, it is possible to provide a medical image processing device, a treatment system, and a medical image processing program which can easily confirm a position of a patient in a patient positioning operation performed before initiation of radiation treatment.

REFERENCE SIGNS LIST

1 Treatment system
10 Treatment device
100, 100A, 100B Medical image processing device
110 Learning device
111 First image acquirer
111a Mask image acquirer
111b Local area setter
112 First position acquirer
113 First converter
114 First likelihood image generator
115 Learner
116 Parameter storage
120, 120A, 120B Moving object tracking device 121 Second image acquirer
122 Second likelihood image generator
123 First estimator
124 Second converter
125 Reliability deriver
126 Second estimator
127 Determiner
128 Storage

The invention claimed is:

1. A medical image processing device comprising:
 a first position acquirer configured to acquire, as first positions, target positions in a plurality of first images that are transparent images at a plurality of points in time at which a patient is imaged;
 a first converter configured to convert the first positions in the plurality of first images to second positions by expanding movement in a second direction intersecting a first direction in which movement over time of the first positions is large;
 a first likelihood image generator configured to generate a first likelihood image showing a distribution of likelihood indicating probability of corresponding to the second positions on the basis of the second positions; and
 a learner configured to output a model which uses some or all of the plurality of first images and the first likelihood image as training data, and upon receiving part or all of a transparent image, derives a second likelihood image showing a distribution of likelihood indicating probability of the part or all of the transparent image corresponding to the second positions.

2. The medical image processing device according to claim 1, further comprising:
 a second image acquirer configured to acquire second images that are the transparent images captured at different points in time from the points in time at which the first images are captured;
 a second likelihood image generator configured to generate the second likelihood image by inputting some or all of the second images to the model;
 a first estimator configured to estimate second positions in the second images on the basis of the second likelihood image; and
 a second converter configured to convert the second positions estimated by the first estimator in a direction reverse to conversion performed by the first convener and output the converted second positions as target positions of the patient in the second images.

3. The medical image processing device according to claim 2, further comprising a reliability deriver configured to derive reliability of the second positions on the basis of the distribution of likelihood in the second likelihood image.

4. The medical image processing device according to claim 3, further comprising a second estimator configured to extract partial images associated with the first positions or the second positions in the second images or positions reversely converted from the second positions on the basis of the reliability, cause a storage to store the partial images, and estimate target positions of the patient in the second images on the basis of a degree of matching between some of the second images and the partial images.

5. The medical image processing device according to claim 4, further comprising a third estimator configured to estimate third positions on the basis of the target positions of the patient output from the second converter, the target position of the patient estimated by the second estimator, the reliability, and the degree of matching.

6. The medical image processing device according to claim 1, wherein the first converter is configured to convert the first positions to the second positions using a transformation matrix set on the basis of movement over time of the first positions.

7. The medical image processing device according to claim 2, further comprising a local area setter configured to set one or local areas of the first images on the basis of pixel values of the first images,
 wherein at least one of the local areas is associated with the first likelihood image, and
 the learner is configured to regressively learn the second likelihood image using an image of the local area with which the first likelihood image is not associated and an image of the local area with which the first likelihood image is associated as training data.

8. The medical image processing device according to claim 7, wherein the local area setter is configured to set the local areas associated with the first likelihood image to include a trajectory of the first positions in a plurality of first images having different respiration phases and set the local areas on the basis of luminance of the first images.

9. The medical image processing device according to claim 7, further comprising a mask image acquirer configured to acquire a mask image representing an area in which a subject that is not a main subject of the transparent images is captured in the first images,
 wherein the local area setter is configured to select a local area in which the area where the subject is captured is small, represented by the mask image.

10. A medical image processing method, using a computer, comprising:
 acquiring first positions from a plurality of first images that are transparent images at a plurality of points in time at which a patient is imaged;
 converting the plurality of first positions to a plurality of second positions by expanding a distribution of the plurality of first positions acquired from the plurality of first images in a second direction intersecting a first direction in which movement of the first positions is large;
 generating a first likelihood image on the basis of the plurality of second positions; and
 outputting a model which has regressively learned the first likelihood image from the transparent images and derives a likelihood image of the first positions upon receiving the transparent images.

11. A non-transitory computer-readable storage medium that stores a program causing a computer to:
 acquire first positions from a plurality of first images that are transparent images at a plurality of points in time at which a patient is imaged;
 convert the plurality of first positions to a plurality of second positions by expanding a distribution of the plurality of first positions acquired from the plurality of first images in a second direction intersecting a first direction in which movement of the first positions is large;
 generate a first likelihood image on the basis of the plurality of second positions; and
 output a model which has regressively learned the first likelihood image from the transparent images and derives a likelihood image of the first positions upon receiving the transparent images.

* * * * *